United States Patent
Peters et al.

(10) Patent No.: US 8,173,658 B2
(45) Date of Patent: May 8, 2012

(54) DIAZABICYCYLIC ARYL DERIVATIVES AND THEIR MEDICAL USE

(75) Inventors: Dan Peters, Malmö (SE); Daniel B. Timmermann, Herlev (DK); Gunnar M. Olsen, Smørum (DK); Elsebet Østergaard Nielsen, København K (DK); Tino Dyhring, Solrød (DK)

(73) Assignee: Neurosearch A/S, Ballerup (DK)

( * ) Notice: Subject to any disclaimer, the term of this patent is extended or adjusted under 35 U.S.C. 154(b) by 1013 days.

(21) Appl. No.: 12/093,655

(22) PCT Filed: Dec. 5, 2006

(86) PCT No.: PCT/EP2006/069316
§ 371 (c)(1),
(2), (4) Date: May 14, 2008

(87) PCT Pub. No.: WO2007/065892
PCT Pub. Date: Jun. 14, 2007

(65) Prior Publication Data
US 2008/0280912 A1  Nov. 13, 2008

(30) Foreign Application Priority Data
Dec. 6, 2005  (DK) .................................. 2005 01724

(51) Int. Cl.
C07D 403/04  (2006.01)
A61K 31/501  (2006.01)
A61P 25/28  (2006.01)
A61P 29/00  (2006.01)
A61P 25/04  (2006.01)

(52) U.S. Cl. .................................. 514/252.02; 544/238

(58) Field of Classification Search .................. 544/238; 514/252.02
See application file for complete search history.

(56) References Cited

U.S. PATENT DOCUMENTS

| | | |
|---|---|---|
| 3,293,251 A | 12/1966 | Cignarella et al. |
| 5,478,939 A | 12/1995 | Trybulski et al. |
| 2003/0225268 A1 | 12/2003 | Bunnelle et al. |
| 2005/0096327 A1 | 5/2005 | Caprathe et al. |
| 2005/0101602 A1 | 5/2005 | Basha et al. |
| 2011/0077400 A1* | 3/2011 | Lobben et al. ................. 544/238 |

FOREIGN PATENT DOCUMENTS

| | | |
|---|---|---|
| WO | WO-98/54181 A1 | 12/1998 |
| WO | WO-98/54182 A1 | 12/1998 |
| WO | WO-00/34279 A1 | 6/2000 |
| WO | WO-00/44755 A1 | 8/2000 |
| WO | WO-00/66586 A1 | 11/2000 |
| WO | WO-01/90109 A1 | 11/2001 |
| WO | WO-01/92259 A1 | 12/2001 |
| WO | WO-01/92260 A1 | 12/2001 |
| WO | WO-02/02564 A1 | 1/2002 |
| WO | WO-02/096911 A1 | 12/2002 |
| WO | WO-03/044019 A1 | 5/2003 |
| WO | WO-03/044020 A1 | 5/2003 |
| WO | WO 03/094831 A2 | 11/2003 |
| WO | WO-2004/043960 A1 | 5/2004 |
| WO | WO-2006/045716 A1 | 5/2006 |
| WO | WO-2006/058879 A1 | 6/2006 |
| WO | WO-2006/087306 A2 | 8/2006 |

OTHER PUBLICATIONS

Lucio Toma et al., "6-Chloropyridazin-3-yl Derivatives Active as Nicotinic Agents: Synthesis, Binding, and Modeling Studies", J. Med. Chem. 2002 45 4011-4017.

* cited by examiner

*Primary Examiner* — James O Wilson
*Assistant Examiner* — Cecilia M Jaisle
(74) *Attorney, Agent, or Firm* — Birch, Stewart, Kolasch & Birch, LLP.

(57) ABSTRACT

This invention relates to novel diazabicyclic aryl derivatives, which are found to be cholinergic ligands at the nicotinic acetylcholine receptors and modulators of the monoamine receptors and transporters. Due to their pharmacological profile the compounds of the invention may be useful for the treatment of diseases or disorders as diverse as those related to the cholinergic system of the central nervous system (CNS), the peripheral nervous system (PNS), diseases or disorders related to smooth muscle contraction, endocrine diseases or disorders, diseases or disorders related to neurodegeneration, diseases or disorders related to inflammation, pain, and withdrawal symptoms caused by the termination of abuse of chemical substances.

13 Claims, No Drawings

DIAZABICYCLIC ARYL DERIVATIVES AND THEIR MEDICAL USE

TECHNICAL FIELD

This invention relates to novel diazabicyclic aryl derivatives, which are found to be cholinergic ligands at the nicotinic acetylcholine receptors and modulators of the monoamine receptors and transporters. Due to their pharmacological profile the compounds of the invention may be useful for the treatment of diseases or disorders as diverse as those related to the cholinergic system of the central nervous system (CNS), the peripheral nervous system (PNS), diseases or disorders related to smooth muscle contraction, endocrine diseases or disorders, diseases or disorders related to neurodegeneration, diseases or disorders related to inflammation, pain, and withdrawal symptoms caused by the termination of abuse of chemical substances.

BACKGROUND ART

The endogenous cholinergic neurotransmitter, acetylcholine, exert its biological effect via two types of cholinergic receptors, the muscarinic Acetyl Choline Receptors (mAChR) and the nicotinic Acetyl Choline Receptors (nAChR).

As it is well established that muscarinic acetylcholine receptors dominate quantitatively over nicotinic acetylcholine receptors in the brain area important to memory and cognition, and much research aimed at the development of agents for the treatment of memory related disorders have focused on the synthesis of muscarinic acetylcholine receptor modulators.

Recently, however, an interest in the development of nAChR modulators has emerged. Several diseases are associated with degeneration of the cholinergic system i.e. senile dementia of the Alzheimer type, vascular dementia and cognitive impairment due to the organic brain damage disease related directly to alcoholism. Indeed several CNS disorders can be attributed to a cholinergic deficiency, a dopaminergic deficiency, an adrenergic deficiency or a serotonergic deficiency.

SUMMARY OF THE INVENTION

The present invention is devoted to the provision novel modulators of the nicotinic and/or of the monoamine receptors, which modulators are useful for the treatment of diseases or disorders related to the cholinergic receptors, and in particular the nicotinic acetylcholine receptor (nAChR), the serotonin receptor (5-HTR), the dopamine receptor (DAR) and the norepinephrine receptor (NER), and of the biogenic amine transporters for serotonin (5-HT), dopamine (DA) and norepinephrine (NE).

Due to their pharmacological profile the compounds of the invention may be useful for the treatment of diseases or disorders as diverse as those related to the cholinergic system of the central nervous system (CNS), the peripheral nervous system (PNS), diseases or disorders related to smooth muscle contraction, endocrine diseases or disorders, diseases or disorders related to neuro-degeneration, diseases or disorders related to inflammation, pain, and withdrawal symptoms caused by the termination of abuse of chemical substances.

The compounds of the invention may also be useful as diagnostic tools or monitoring agents in various diagnostic methods, and in particular for in vivo receptor imaging (neuroimaging), and they may be used in labelled or unlabelled form.

In its first aspect the invention provides novel diazabicyclic aryl derivatives of Formula I

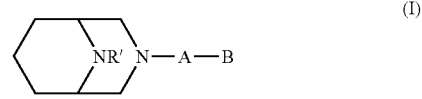

any of its enantiomers or any mixture of its enantiomers, or a pharmaceutically acceptable salt thereof, wherein R' represents hydrogen, alkyl, alkenyl or alkoxy-alkyl;

A represents an aromatic monocyclic group selected from phenyl, furanyl, thienyl, selenophenyl, pyrrolyl, oxazolyl, thiazolyl, imidazolyl, pyrazolyl, isoxazolyl, isothiazolyl, oxadiazolyl, triazolyl, thiadiazolyl, pyridinyl, pyridazinyl, pyrimidinyl, pyrazinyl and triazinyl; and B represents an aromatic monocyclic or bicyclic carbocyclic or heterocyclic group, which carbocyclic or heterocyclic groups are optionally substituted one or more times with substituents selected from the group consisting of alkyl, cycloalkyl, cycloalkyl-alkyl, hydroxy, alkoxy, cyanoalkyl, halo, trihaloalkyl, trihaloalkoxy, cyano, nitro, amino, alkyl-carbonyl-amino, methylenedioxy and ethylenedioxy.

In its second aspect the invention provides pharmaceutical compositions comprising a therapeutically effective amount of the diazabicyclic aryl derivative of the invention, or a pharmaceutically-acceptable addition salt thereof, or a pro-drug thereof, together with at least one pharmaceutically-acceptable carrier or diluent.

In a further aspect the invention relates to the use of the diazabicyclic aryl derivative of the invention, or a pharmaceutically-acceptable addition salt thereof, for the manufacture of a pharmaceutical composition/medicament for the treatment, prevention or alleviation of a disease or a disorder or a condition of a mammal, including a human, which disease, disorder or condition is responsive to modulation of cholinergic receptors and/or monoamine receptors.

In a final aspect the invention provides methods of treatment, prevention or alleviation of diseases, disorders or conditions of a living animal body, including a human, which disorder, disease or condition is responsive to modulation of cholinergic receptors and/or monoamine receptors, which method comprises the step of administering to such a living animal body in need thereof a therapeutically effective amount of the diazabicyclic aryl derivative of the invention.

Other objects of the invention will be apparent to the person skilled in the art from the following detailed description and examples.

DETAILED DISCLOSURE OF THE INVENTION

Diazabicyclic Aryl Derivatives

In a first aspect novel 3,9-diaza-bicyclo[3.3.1]octane aryl derivatives are provided. The diazabicyclic aryl derivatives of the invention may be represented by the general Formula I

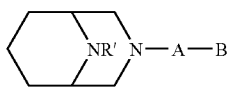 (I)

any of its enantiomers or any mixture of its enantiomers, or a pharmaceutically acceptable salt thereof, wherein R' represents hydrogen, alkyl, alkenyl or alkoxy-alkyl;

A represents an aromatic monocyclic group selected from phenyl, furanyl, thienyl, selenophenyl, pyrrolyl, oxazolyl, thiazolyl, imidazolyl, pyrazolyl, isoxazolyl, isothiazolyl, oxadiazolyl, triazolyl, thiadiazolyl, pyridinyl, pyridazinyl, pyrimidinyl, pyrazinyl and triazinyl; and B represents an aromatic monocyclic or bicyclic carbocyclic or heterocyclic group, which carbocyclic or heterocyclic groups are optionally substituted one or more times with substituents selected from the group consisting of alkyl, cycloalkyl, cycloalkyl-alkyl, hydroxy, alkoxy, cyanoalkyl, halo, trihaloalkyl, trihaloalkoxy, cyano, nitro, amino, alkyl-carbonyl-amino, methylenedioxy and ethylenedioxy.

In a preferred embodiment the diazabicyclic aryl derivative of the invention is a compound of Formula I, wherein R' represents hydrogen, or alkyl, alkenyl or alkoxy-alkyl.

In a more preferred embodiment R' represents hydrogen or alkyl.

In an even more preferred embodiment R' represents hydrogen, methyl, ethyl, propyl, allyl, methoxy-methyl or methoxy-ethyl.

In a still more preferred embodiment R' represents hydrogen, methyl, ethyl, propyl, allyl or methoxy-ethyl.

In a yet more preferred embodiment R' represents hydrogen, methyl, ethyl or propyl.

In a further more preferred embodiment R' represents hydrogen or methyl.

In a still further more preferred embodiment R' represents allyl or methoxy-ethyl.

In another preferred embodiment the diazabicyclic aryl derivative of the invention is a compound of Formula I, wherein R' represents alkyl.

In a more preferred embodiment R' represents methyl, ethyl or propyl.

In an even more preferred embodiment R' represents methyl.

In a third preferred embodiment the diazabicyclic aryl derivative of the invention is a compound of Formula I, wherein A represents an aromatic monocyclic group selected from phenyl, furanyl, thienyl, selenophenyl, pyrrolyl, oxazolyl, thiazolyl, imidazolyl, pyrazolyl, isoxazolyl, isothiazolyl, oxadiazolyl, triazolyl, thiadiazolyl, pyridinyl, pyridazinyl, pyrimidinyl, pyrazinyl and triazinyl.

In a fourth preferred embodiment the diazabicyclic aryl derivative of the invention is a compound of Formula I, wherein A represents an aromatic heterocyclic group selected from furanyl, thienyl, selenophenyl, pyrrolyl, oxazolyl, thiazolyl, imidazolyl, pyrazolyl, isoxazolyl, isothiazolyl, oxadiazolyl, triazolyl, thiadiazolyl, pyridinyl, pyridazinyl, pyrimidinyl, pyrazinyl and triazinyl.

In a fifth preferred embodiment the diazabicyclic aryl derivative of the invention is a compound of Formula I, wherein A represents oxazolyl, thiazolyl, oxadiazolyl, thiadiazolyl, pyridinyl, pyridazinyl, pyrimidinyl or pyrazinyl.

In a more preferred embodiment A represents oxadiazolyl, thiadiazolyl, pyridazinyl or pyrimidinyl.

In an even more preferred embodiment A represents 1,3,4-oxadiazolyl, 1,3,4-thiadiazolyl, pyridazinyl or pyrimidinyl.

In a still more preferred embodiment A represents pyridazinyl.

In a yet more preferred embodiment A represents pyridazin-3,6-diyl.

In a further more preferred embodiment A represents 1,3,4-oxadiazol-2,5-diyl.

In a still further more preferred embodiment A represents 1,3,4-thiadiazol-2,5-diyl.

In a still further more preferred embodiment A represents pyrimidin-2,5-diyl.

In a sixth preferred embodiment the diazabicyclic aryl derivative of the invention is a compound of Formula I, wherein B represents an aromatic monocyclic or bicyclic carbocyclic or heterocyclic group, which carbocyclic or heterocyclic groups are optionally substituted one or more times with substituents selected from the group consisting of alkyl, cycloalkyl, cycloalkyl-alkyl, hydroxy, alkoxy, cyanoalkyl, halo, trihaloalkyl, trihaloalkoxy, cyano, nitro, amino, alkyl-carbonyl-amino, methylenedioxy and ethylenedioxy.

In a more preferred embodiment B represents an aromatic monocyclic or bicyclic carbocyclic or heterocyclic group, which carbocyclic or heterocyclic groups are optionally substituted one or more times with substituents selected from the group consisting of alkyl, cycloalkyl, cycloalkyl-alkyl, hydroxy, alkoxy, cyanoalkyl, halo, trihaloalkyl, trihaloalkoxy, cyano, nitro, amino and alkyl-carbonyl-amino.

In a seventh preferred embodiment the diazabicyclic aryl derivative of the invention is a compound of Formula I, wherein B represents an aromatic monocyclic or bicyclic carbocyclic or heterocyclic group selected from phenyl, naphthyl, pyrrolyl, furanyl, thienyl, indolyl, benzofuranyl and benzothienyl, which carbocyclic or heterocyclic groups are optionally substituted one or more times with substituents selected from the group consisting of alkyl, cycloalkyl, cycloalkyl-alkyl, hydroxy, alkoxy, cyanoalkyl, halo, trihaloalkyl, trihaloalkoxy, cyano, nitro, amino, alkyl-carbonyl-amino, methylenedioxy and ethylenedioxy.

In a more preferred embodiment B represents an aromatic monocyclic or bicyclic carbocyclic or heterocyclic group selected from phenyl, naphthyl, pyrrolyl, furanyl, thienyl, indolyl, benzofuranyl and benzothienyl, which carbocyclic or heterocyclic groups are optionally substituted one or more times with substituents selected from the group consisting of hydroxy, alkoxy, halo, trihaloalkyl, amino, methylenedioxy and ethylenedioxy.

In an even more preferred embodiment B represents an aromatic monocyclic or bicyclic carbocyclic or heterocyclic group selected from phenyl, naphthyl, pyrrolyl, furanyl, thienyl, indolyl, benzofuranyl and benzothienyl, which carbocyclic or heterocyclic groups are optionally substituted one or two times with substituents selected from the group consisting of hydroxy, alkoxy, halo, trihaloalkyl, amino, methylenedioxy and ethylenedioxy.

In a yet more preferred embodiment B represents an aromatic monocyclic or bicyclic carbocyclic or heterocyclic group selected from phenyl, naphthyl, pyrrolyl, furanyl, thienyl, indolyl, benzofuranyl and benzothienyl, which carbocyclic or heterocyclic groups are optionally substituted one or two times with substituents selected from the group consisting of methoxy, fluoro, chloro, trifluoromethyl, amino, methylenedioxy and ethylenedioxy.

In a further more preferred embodiment B represents phenyl or naphthyl, which carbocyclic groups are optionally substituted one or more times with substituents selected from the group consisting of alkyl, cycloalkyl, cycloalkyl-alkyl, hydroxy, alkoxy, cyanoalkyl, halo, trihaloalkyl, trihaloalkoxy, cyano, nitro, amino, alkyl-carbonyl-amino, methylenedioxy and ethylenedioxy.

In a still further more preferred embodiment B represents phenyl or naphthyl, which carbocyclic groups are optionally substituted one or more times with substituents selected from the group consisting of alkyl, cycloalkyl, cycloalkyl-alkyl, hydroxy, alkoxy, cyanoalkyl, halo, trihaloalkyl, trihaloalkoxy, cyano, nitro, amino and alkyl-carbonyl-amino.

In a still further more preferred embodiment B represents phenyl or naphthyl, which carbocyclic group is optionally substituted one or more times with substituents selected from the group consisting of alkyl, cycloalkyl, cycloalkyl-alkyl, hydroxy, alkoxy, cyanoalkyl, halo, trihaloalkyl, trihaloalkoxy, cyano, nitro, amino and alkyl-carbonyl-amino.

In a still further more preferred embodiment B represents phenyl or naphthyl.

In a still further more preferred embodiment B represents phenyl.

In an eight preferred embodiment the diazabicyclic aryl derivative of the invention is a compound of Formula I, wherein B represents phenyl or naphthyl, which phenyl and naphthyl are unsubstituted or substituted once or twice with halo, alkoxy and/or amino, or substituted with methylenedioxy or with ethylenedioxy.

In a ninth preferred embodiment the diazabicyclic aryl derivative of the invention is a compound of Formula I, wherein B represents pyrrolyl, furanyl or thienyl, which pyrrolyl, furanyl or thienyl are unsubstituted or substituted once with halo.

In a tenth preferred embodiment the diazabicyclic aryl derivative of the invention is a compound of Formula I, wherein B represents indolyl, benzofuranyl and benzothienyl, which indolyl, benzofuranyl and benzothienyl are unsubstituted.

In a more preferred embodiment B represents indol-5-yl, benzofuran-2-yl or benzothien-2-yl.

In a most preferred embodiment the diazabicyclic aryl derivative of the invention is
9-Methyl-3-(6-phenyl-pyridazin-3-yl)-3,9-diaza-bicyclo[3.3.1]nonane;
3-(6-Phenyl-pyridazin-3-yl)-3,9-diaza-bicyclo[3.3.1]nonane;
9-Methyl-3-(5-phenyl-[1,3,4]oxadiazol-2-yl)-3,9-diaza-bicyclo[3.3.1]nonane;
9-Methyl-3-(5-phenyl-[1,3,4]thiadiazol-2-yl)-3,9-diaza-bicyclo[3.3.1]nonane;
3-[5-(4-Chloro-phenyl)-[1,3,4]thiadiazol-2-yl]-9-methyl-3,9-diaza-bicyclo[3.3.1]nonane;
9-Methyl-3-(6-thiophen-3-yl-pyridazin-3-yl)-3,9-diaza-bicyclo[3.3.1]nonane;
9-Methyl-3-(6-thiophen-2-yl-pyridazin-3-yl)-3,9-diaza-bicyclo[3.3.1]nonane;
3-(6-Furan-2-yl-pyridazin-3-yl)-9-methyl-3,9-diaza-bicyclo[3.3.1]nonane;
3-(6-Furan-3-yl-pyridazin-3-yl)-9-methyl-3,9-diaza-bicyclo[3.3.1]nonane;
3-[6-(3-Fluoro-phenyl)-pyridazin-3-yl]-9-methyl-3,9-diaza-bicyclo[3.3.1]nonane;
3-[6-(4-Fluoro-phenyl)-pyridazin-3-yl]-9-methyl-3,9-diaza-bicyclo[3.3.1]nonane;
3-[6-(2-Methoxy-phenyl)-pyridazin-3-yl]-9-methyl-3,9-diaza-bicyclo[3.3.1]nonane;
3-[6-(3-Methoxy-phenyl)-pyridazin-3-yl]-9-methyl-3,9-diaza-bicyclo[3.3.1]nonane;
3-[6-(2-Fluoro-phenyl)-pyridazin-3-yl]-9-methyl-3,9-diaza-bicyclo[3.3.1]nonane;
3-[6-(4-Methoxy-phenyl)-pyridazin-3-yl]-9-methyl-3,9-diaza-bicyclo[3.3.1]nonane;
3-[6-(9-Methyl-3,9-diaza-bicyclo[3.3.1]non-3-yl)-pyridazin-3-yl]-phenylamine;
3-[6-(5-Chloro-thiophen-2-yl)-pyridazin-3-yl]-9-methyl-3,9-diaza-bicyclo[3.3.1]nonane;
9-Methyl-3-[6-(1H-pyrrol-2-yl)-pyridazin-3-yl]-3,9-diaza-bicyclo[3.3.1]nonane;
3-[6-(1H-Indol-5-yl)-pyridazin-3-yl]-9-methyl-3,9-diaza-bicyclo[3.3.1]nonane;
3-(6-Benzo[1,3]dioxol-5-yl-pyridazin-3-yl)-9-methyl-3,9-diaza-bicyclo[3.3.1]nonane;
3-[6-(2,3-Dihydro-benzo[1,4]dioxin-6-yl)-pyridazin-3-yl]-9-methyl-3,9-diaza-bicyclo[3.3.1]nonane;
3-[6-(4-Chloro-phenyl)-pyridazin-3-yl]-9-methyl-3,9-diaza-bicyclo[3.3.1]nonane;
3-[6-(3-Chloro-phenyl)-pyridazin-3-yl]-9-methyl-3,9-diaza-bicyclo[3.3.1]nonane;
9-Methyl-3-(6-naphthalen-2-yl-pyridazin-3-yl)-3,9-diaza-bicyclo[3.3.1]nonane;
3-(6-Benzofuran-2-yl-pyridazin-3-yl)-9-methyl-3,9-diaza-bicyclo[3.3.1]nonane;
3-(6-Benzo[b]thiophen-2-yl-pyridazin-3-yl)-9-methyl-3,9-diaza-bicyclo[3.3.1]nonane;
3-[6-(3,4-Difluoro-phenyl)-pyridazin-3-yl]-9-methyl-3,9-diaza-bicyclo[3.3.1]nonane;
3-[6-(2,3-Difluoro-phenyl)-pyridazin-3-yl]-9-methyl-3,9-diaza-bicyclo[3.3.1]nonane;
3-[6-(3,4-Dimethoxy-phenyl)-pyridazin-3-yl]-9-methyl-3,9-diaza-bicyclo[3.3.1]nonane;
3-[6-(2,3-Dimethoxy-phenyl)-pyridazin-3-yl]-9-methyl-3,9-diaza-bicyclo[3.3.1]nonane;
9-Methyl-3-[6-(4-trifluoromethyl-phenyl)-pyridazin-3-yl]-3,9-diaza-bicyclo[3.3.1]nonane;
9-Methyl-3-[6-(3-trifluoromethyl-phenyl)-pyridazin-3-yl]-3,9-diaza-bicyclo[3.3.1]nonane;
9-Methyl-3-(5-thiophen-2-yl-pyrimidin-2-yl)-3,9-diaza-bicyclo[3.3.1]nonane;
9-Methyl-3-(5-thiophen-3-yl-pyrimidin-2-yl)-3,9-diaza-bicyclo[3.3.1]nonane;
3-(5-Furan-3-yl-pyrimidin-2-yl)-9-methyl-3,9-diaza-bicyclo[3.3.1]nonane;
3-(5-Furan-2-yl-pyrimidin-2-yl)-9-methyl-3,9-diaza-bicyclo[3.3.1]nonane;
9-Methyl-3-(5-phenyl-pyrimidin-2-yl)-3,9-diaza-bicyclo[3.3.1]nonane;
9-Methyl-3-(5-naphthalen-2-yl-pyrimidin-2-yl)-3,9-diaza-bicyclo[3.3.1]nonane;
3-(5-Benzofuran-2-yl-pyrimidin-2-yl)-9-methyl-3,9-diaza-bicyclo[3.3.1]nonane;
3-[5-(1H-Indol-5-yl)-pyrimidin-2-yl]-9-methyl-3,9-diaza-bicyclo[3.3.1]nonane;
9-Ethyl-3-(6-phenyl-pyridazin-3-yl)-3,9-diaza-bicyclo[3.3.1]nonane;
9-(2-Methoxy-ethyl)-3-(6-phenyl-pyridazin-3-yl)-3,9-diaza-bicyclo[3.3.1]nonane;
9-Isopropyl-3-(6-phenyl-pyridazin-3-yl)-3,9-diaza-bicyclo[3.3.1]nonane;
9-Allyl-3-(6-phenyl-pyridazin-3-yl)-3,9-diaza-bicyclo[3.3.1]nonane; or
9,9-Dimethyl-3-(6-phenyl-pyridazin-3-yl)-3,9-diaza-bicyclo[3.3.1]nonane;
or an enantiomer or a mixture of its enantiomers, or a pharmaceutically acceptable salt thereof.

Any combination of two or more of the embodiments described herein is considered within the scope of the present invention.

Definition of Substituents

In the context of this invention halo represents a fluorine, a chlorine, a bromine or an iodine atom. Thus, a trihalomethyl group represents e.g. a trifluoromethyl group, a trichloromethyl group and similar trihalo-substituted methyl groups.

In the context of this invention an alkyl group designates a univalent saturated, straight or branched hydrocarbon chain. The hydrocarbon chain preferably contain of from one to eighteen carbon atoms ($C_{1-18}$-alkyl), more preferred of from one to six carbon atoms ($C_{1-6}$-alkyl; lower alkyl), including pentyl, isopentyl, neopentyl, tertiary pentyl, hexyl and isohexyl. In a preferred embodiment alkyl represents a $C_{1-4}$-alkyl group, including butyl, isobutyl, secondary butyl, and tertiary butyl. In another preferred embodiment of this invention alkyl represents a $C_{1-3}$-alkyl group, which may in particular be methyl, ethyl, propyl or isopropyl.

In the context of this invention a cycloalkyl group designates a cyclic alkyl group, preferably containing of from three to seven carbon atoms ($C_{3-7}$-cycloalkyl), including cyclopropyl, cyclobutyl, cyclopentyl, cyclohexyl and cycloheptyl.

In the context of this invention a cycloalkyl-alkyl group designates a cycloalkyl group as defined above, which cycloalkyl group is substituted on an alkyl group as also defined above. Examples of preferred cycloalkyl-alkyl groups of the invention include cyclopropylmethyl and cyclopropylethyl.

In the context of this invention an alkoxy group designates an "alkyl-O—" group, wherein alkyl is as defined above. Examples of preferred alkoxy groups of the invention include methoxy and ethoxy.

In the context of this invention a cyanoalkyl group designates an "-alkyl-CN" group, wherein alkyl is as defined above.

In the context of this invention an alkyl-carbonyl-amino group designates an "alkyl-CO—NH—" group, wherein alkyl is as defined above. Preferred alkyl-carbonyl-amino groups of the invention include acetamido.

In the context of this invention an aromatic monocyclic or bicyclic carbocyclic group designates a monocyclic or polycyclic aromatic hydrocarbon group. Examples of preferred aryl groups of the invention include phenyl, indenyl, naphthyl, azulenyl, fluorenyl, and anthracenyl.

In the context of this invention an aromatic monocyclic or bicyclic heterocyclic group is a mono- or bicyclic compound, which holds one or more heteroatoms in its ring structure. The term "bi- and poly-heterocyclic groups" includes benzo-fused five- and six-membered heterocyclic rings containing one or more heteroatoms. Preferred heteroatoms include nitrogen (N), oxygen (O), and sulphur (S).

In the context of this invention a 5-6 membered aromatic monocyclic heterocyclic designates a 5- or 6-membered heteroaryl, which holds one or more heteroatoms in its ring structure. Preferred heteroatoms include nitrogen (N), oxygen (O), and sulphur (S).

Preferred 5 membered heteroaryl groups of the invention include furanyl, in particular furan-2- or 3-yl; thienyl, in particular thein-2- or 3-yl; pyrrolyl (azolyl), in particular pyrrol-2- or 3-yl; oxazolyl, in particular oxazol-2, 4- or 5-yl; thiazolyl, in particular thiazol-2, 4- or 5-yl; isoxazolyl, in particular isoxazol-3, 4- or 5-yl; isothiazolyl, in particular isothiazol-3-, 4- or 5-yl; oxadiazolyl, in particular 1,2,3-oxadiazol-4,5-diyl or 1,3,4-oxadiazol-2,5-diyl and thiadiazolyl, in particular 1,2,3-thiadiazol-4- or 5-yl, or 1,3,4-thiadiazol-2-yl.

More preferred 5 membered heteroaryl groups of the invention include oxadiazolyl, in particular 1,2,3-oxadiazol-4,5-diyl or 1,3,4-oxadiazol-2,5-diyl and thiadiazolyl, in particular 1,2,3-thiadiazol-4- or 5-yl, or 1,3,4-thiadiazol-2-yl.

Preferred 6 membered heteroaryl groups of the invention include pyridinyl, in particular pyrid-2-, 3- or 4-yl; and pyrazinyl, in particular pyrazin-2- or 3-yl.

Preferred bicyclic heteroaryl groups of the invention include indolyl, in particular indol-2-, 5- or 6-yl; benzo[b]furanyl, in particular benzofuran-2-, 5- or 6-yl; benzo[b]thienyl, in particular benzothien-2-, 5- or 6-yl; and benzothiazolyl, in particular benzothiazol-2-, 5- or 6-yl.

Pharmaceutically Acceptable Salts

The diazabicyclic aryl derivative of the invention may be provided in any form suitable for the intended administration. Suitable forms include pharmaceutically (i.e. physiologically) acceptable salts, and pre- or prodrug forms of the chemical compound of the invention.

Examples of pharmaceutically acceptable addition salts include, without limitation, the non-toxic inorganic and organic acid addition salts such as the hydrochloride derived from hydrochloric acid, the hydrobromide derived from hydrobromic acid, the nitrate derived from nitric acid, the perchlorate derived from perchloric acid, the phosphate derived from phosphoric acid, the sulphate derived from sulphuric acid, the formate derived from formic acid, the acetate derived from acetic acid, the aconate derived from aconitic acid, the ascorbate derived from ascorbic acid, the benzenesulphonate derived from benzensulphonic acid, the benzoate derived from benzoic acid, the cinnamate derived from cinnamic acid, the citrate derived from citric acid, the embonate derived from embonic acid, the enantate derived from enanthic acid, the fumarate derived from fumaric acid, the glutamate derived from glutamic acid, the glycolate derived from glycolic acid, the lactate derived from lactic acid, the maleate derived from maleic acid, the malonate derived from malonic acid, the mandelate derived from mandelic acid, the methanesulphonate derived from methane sulphonic acid, the naphthalene-2-sulphonate derived from naphtalene-2-sulphonic acid, the phthalate derived from phthalic acid, the salicylate derived from salicylic acid, the sorbate derived from sorbic acid, the stearate derived from stearic acid, the succinate derived from succinic acid, the tartrate derived from tartaric acid, the toluene-p-sulphonate derived from p-toluene sulphonic acid, and the like. Such salts may be formed by procedures well known and described in the art.

Other examples of pharmaceutically acceptable addition salts include, without limitation, the non-toxic inorganic and organic acid addition salts such as the hydrochloride, the hydrobromide, the nitrate, the perchlorate, the phosphate, the sulphate, the formate, the acetate, the aconate, the ascorbate, the benzenesulphonate, the benzoate, the cinnamate, the citrate, the embonate, the enantate, the fumarate, the glutamate, the glycolate, the lactate, the maleate, the malonate, the mandelate, the methanesulphonate, the naphthalene-2-sulphonate derived, the phthalate, the salicylate, the sorbate, the stearate, the succinate, the tartrate, the toluene-p-sulphonate, and the like. Such salts may be formed by procedures well known and described in the art.

Other acids such as oxalic acid, which may not be considered pharmaceutically acceptable, may be useful in the preparation of salts useful as intermediates in obtaining a chemical compound of the invention and its pharmaceutically acceptable acid addition salt.

Metal salts of a chemical compound of the invention include alkali metal salts, such as the sodium salt of a chemical compound of the invention containing a carboxy group.

In the context of this invention the "onium salts" of N-containing compounds are also contemplated as pharmaceutically acceptable salts. Preferred "onium salts" include the alkyl-onium salts, the cycloalkyl-onium salts, and the cycloalkylalkyl-onium salts.

Steric Isomers

The chemical compounds of the present invention may exist in (+) and (−) forms as well as in racemic forms. The racemates of these isomers and the individual isomers themselves are within the scope of the present invention.

Racemic forms can be resolved into the optical antipodes by known methods and techniques. One way of separating the diastereomeric salts is by use of an optically active acid, and liberating the optically active amine compound by treatment with a base. Another method for resolving racemates into the optical antipodes is based upon chromatography on an optical active matrix. Racemic compounds of the present invention can thus be resolved into their optical antipodes, e.g., by fractional crystallisation of d- or l- (tartrates, mandelates, or camphorsulphonate) salts for example.

The chemical compounds of the present invention may also be resolved by the formation of diastereomeric amides by reaction of the chemical compounds of the present invention with an optically active activated carboxylic acid such as that derived from (+) or (−) phenylalanine, (+) or (−) phenylglycine, (+) or (−) camphanic acid or by the formation of diastereomeric carbamates by reaction of the chemical compound of the present invention with an optically active chloroformate or the like.

Additional methods for the resolving the optical isomers are known in the art. Such methods include those described by Jaques J, Collet A, & Wilen S in "*Enantiomers, Racemates, and Resolutions*", John Wiley and Sons, New York (1981).

Optical active compounds can also be prepared from optical active starting materials.

Methods of Producing Diazabicyclic Aryl Derivatives

The diazabicyclic aryl derivative of the invention may be prepared by conventional methods for chemical synthesis, e.g. those described in the working examples. The starting materials for the processes described in the present application are known or may readily be prepared by conventional methods from commercially available chemicals.

Also one compound of the invention can be converted to another compound of the invention using conventional methods.

The end products of the reactions described herein may be isolated by conventional techniques, e.g. by extraction, crystallisation, distillation, chromatography, etc.

Biological Activity

The present invention is devoted to the provision novel ligands and modulators of the nicotinic receptors, which ligands and modulators are useful for the treatment of diseases or disorders related to the cholinergic receptors, and in particular the nicotinic acetylcholine receptor (nAChR). Preferred compounds of the invention show a pronounced nicotinic acetylcholine α7 receptor subtype selectivity.

The compounds of the present invention may in particular be agonists, partial agonists, antagonists and/or allosteric modulators of the nicotinic acetylcholine receptor.

Due to their pharmacological profile the compounds of the invention may be useful for the treatment of diseases or conditions as diverse as CNS related diseases, PNS related diseases, diseases related to smooth muscle contraction, endocrine disorders, diseases related to neuro-degeneration, diseases related to inflammation, pain, and withdrawal symptoms caused by the termination of abuse of chemical substances.

In a preferred embodiment the compounds of the invention are used for the treatment of diseases, disorders, or conditions relating to the central nervous system. Such diseases or disorders includes anxiety, cognitive disorders, learning deficit, memory deficits and dysfunction, Alzheimer's disease, attention deficit, attention deficit hyperactivity disorder, Parkinson's disease, Huntington's disease, Amyotrophic Lateral Sclerosis, Gilles de la Tourette's syndrome, depression, mania, manic depression, schizophrenia, obsessive compulsive disorders (OCD), panic disorders, eating disorders such as anorexia nervosa, bulimia and obesity, narcolepsy, nociception, AIDS-dementia, senile dementia, periferic neuropathy, autism, dyslexia, tardive dyskinesia, hyperkinesia, epilepsy, bulimia, post-traumatic syndrome, social phobia, sleeping disorders, pseudodementia, Ganser's syndrome, pre-menstrual syndrome, late luteal phase syndrome, chronic fatigue syndrome, mutism, trichotillomania, and jet-lag.

In another preferred embodiment the compounds of the invention may be useful for the treatment of diseases, disorders, or conditions associated with smooth muscle contractions, including convulsive disorders, angina pectoris, premature labour, convulsions, diarrhoea, asthma, epilepsy, tardive dyskinesia, hyperkinesia, premature ejaculation, and erectile difficulty.

In yet another preferred embodiment the compounds of the invention may be useful for the treatment of endocrine disorders, such as thyrotoxicosis, pheochromocytoma, hypertension and arrhythmias.

In still another preferred embodiment the compounds of the invention may be useful for the treatment of neurodegenerative disorders, including transient anoxia and induced neuro-degeneration.

In even another preferred embodiment the compounds of the invention may be useful for the treatment of inflammatory diseases, disorders, or conditions, including inflammatory skin disorders such as acne and rosacea, Chron's disease, inflammatory bowel disease, ulcerative colitis, and diarrhoea.

In still another preferred embodiment the compounds of the invention may be useful for the treatment of mild, moderate or even severe pain of acute, chronic or recurrent character, pain caused by migraine, postoperative pain, phantom limb pain, inflammatory pain, chronic headache, central pain, neuropathic pain, pain related to diabetic neuropathy, to post therapeutic neuralgia, or to peripheral nerve injury.

In a further preferred embodiment the compounds of the invention may be useful for the treatment of diabetic neuropathy, schizophrenia, cognitive or attentional deficits related to schizophrenia, or depression.

Finally the compounds of the invention may be useful for the treatment of withdrawal symptoms caused by termination of use of addictive substances. Such addictive substances include nicotine-containing products such as tobacco, opioids such as heroin, cocaine and morphine, benzodiazepines and benzodiazepine-like drugs, and alcohol. Withdrawal from addictive substances is in general a traumatic experience characterised by anxiety and frustration, anger, anxiety, difficulties in concentrating, restlessness, decreased heart rate and increased appetite and weight gain.

In this context "treatment" covers treatment, prevention, prophylactics and alleviation of withdrawal symptoms and abstinence as well as treatment resulting in a voluntary diminished intake of the addictive substance.

In another aspect, the compounds of the invention are used as diagnostic agents, e.g. for the identification and localisation of nicotinic receptors in various tissues.

Pharmaceutical Compositions

In another aspect the invention provides novel pharmaceutical compositions comprising a therapeutically effective amount of diazabicyclic aryl derivative of the invention.

While a chemical compound of the invention for use in therapy may be administered in the form of the raw chemical compound, it is preferred to introduce the active ingredient, optionally in the form of a physiologically acceptable salt, in a pharmaceutical composition together with one or more adjuvants, excipients, carriers, buffers, diluents, and/or other customary pharmaceutical auxiliaries.

In a preferred embodiment, the invention provides pharmaceutical compositions comprising the diazabicyclic aryl derivative of the invention, or a pharmaceutically acceptable salt or derivative thereof, together with one or more pharmaceutically acceptable carriers therefore, and, optionally, other therapeutic and/or prophylactic ingredients, know and used in the art. The carrier(s) must be "acceptable" in the sense of being compatible with the other ingredients of the formulation and not harmful to the recipient thereof.

The pharmaceutical composition of the invention may be administered by any convenient route, which suits the desired therapy. Preferred routes of administration include oral administration, in particular in tablet, in capsule, in dragé in powder, or in liquid form, and parenteral administration, in particular cutaneous, subcutaneous, intramuscular, or intravenous injection. The pharmaceutical composition of the invention can be manufactured by any skilled person by use of standard methods and conventional techniques appropriate to the desired formulation. When desired, compositions adapted to give sustained release of the active ingredient may be employed.

Pharmaceutical compositions of the invention may be those suitable for oral, rectal, bronchial, nasal, pulmonal, topical (including buccal and sub-lingual), transdermal, vaginal or parenteral (including cutaneous, subcutaneous, intramuscular, intraperitoneal, intravenous, intraarterial, intracerebral, intraocular injection or infusion) administration, or those in a form suitable for administration by inhalation or insufflation, including powders and liquid aerosol administration, or by sustained release systems. Suitable examples of sustained release systems include semipermeable matrices of solid hydrophobic polymers containing the compound of the invention, which matrices may be in form of shaped articles, e.g. films or microcapsules.

The chemical compound of the invention, together with a conventional adjuvant, carrier, or diluent, may thus be placed into the form of pharmaceutical compositions and unit dosages thereof. Such forms include solids, and in particular tablets, filled capsules, powder and pellet forms, and liquids, in particular aqueous or non-aqueous solutions, suspensions, emulsions, elixirs, and capsules filled with the same, all for oral use, suppositories for rectal administration, and sterile injectable solutions for parenteral use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed.

The chemical compound of the present invention can be administered in a wide variety of oral and parenteral dosage forms. It will be obvious to those skilled in the art that the following dosage forms may comprise, as the active component, either a chemical compound of the invention or a pharmaceutically acceptable salt of a chemical compound of the invention.

For preparing pharmaceutical compositions from a chemical compound of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, tablet disintegrating agents, or an encapsulating material.

In powders, the carrier is a finely divided solid, which is in a mixture with the finely divided active component.

In tablets, the active component is mixed with the carrier having the necessary binding capacity in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as a mixture of fatty acid glyceride or cocoa butter, is first melted and the active component is dispersed homogeneously therein, as by stirring. The molten homogenous mixture is then poured into convenient sized moulds, allowed to cool, and thereby to solidify.

Compositions suitable for vaginal administration may be presented as pessaries, tampons, creams, gels, pastes, foams or sprays containing in addition to the active ingredient such carriers as are known in the art to be appropriate.

Liquid preparations include solutions, suspensions, and emulsions, for example, water or water-propylene glycol solutions. For example, parenteral injection liquid preparations can be formulated as solutions in aqueous polyethylene glycol solution.

The chemical compound according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulation agents such as suspending, stabilising and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

Aqueous solutions suitable for oral use can be prepared by dissolving the active component in water and adding suitable colorants, flavours, stabilising and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations, intended for conversion shortly before use to liquid form preparations for oral administration. Such liquid forms include solutions, suspensions, and emulsions. In addition to the active component such preparations may comprise colorants, flavours, stabilisers, buffers, artificial and natural sweeteners, dispersants, thickeners, solubilizing agents, and the like.

For topical administration to the epidermis the chemical compound of the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Compositions suitable for topical administration in the mouth include lozenges comprising the active agent in a flavoured base, usually sucrose and acacia or tragacanth; pastilles comprising the active ingredient in an inert base such as gelatin and glycerine or sucrose and acacia; and mouthwashes comprising the active ingredient in a suitable liquid carrier.

Solutions or suspensions are applied directly to the nasal cavity by conventional means, for example with a dropper, pipette or spray. The compositions may be provided in single or multi-dose form.

Administration to the respiratory tract may also be achieved by means of an aerosol formulation in which the active ingredient is provided in a pressurised pack with a suitable propellant such as a chlorofluorocarbon (CFC) for example dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

In compositions intended for administration to the respiratory tract, including intranasal compositions, the compound will generally have a small particle size for example of the order of 5 microns or less. Such a particle size may be obtained by means known in the art, for example by micronization.

When desired, compositions adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packaged tablets, capsules, and powders in vials or ampoules. Also, the unit dosage form can be a capsule, tablet, cachet, or lozenge itself, or it can be the appropriate number of any of these in packaged form.

Tablets or capsules for oral administration and liquids for intravenous administration and continuous infusion are preferred compositions.

Further details on techniques for formulation and administration may be found in the latest edition of *Remington's Pharmaceutical Sciences* (Maack Publishing Co., Easton, Pa.).

The actual dosage depends on the nature and severity of the disease being treated and is within the discretion of the physician, and it may be varied by titration of the dosage to the particular circumstances of this invention to produce the desired therapeutic effect. However, it is presently contemplated that pharmaceutical compositions containing of from about 0.1 to about 500 mg of active ingredient per individual dose, preferably of from about 1 to about 100 mg, most preferred of from about 1 to about 10 mg, are suitable for therapeutic treatments.

The active ingredient may be administered in one or several doses per day. A satisfactory result can, in certain instances, be obtained at a dosage as low as 0.1 μg/kg i.v. and 1 μg/kg p.o. The upper limit of the dosage range is presently considered to be about 10 mg/kg i.v. and 100 mg/kg p.o. Preferred ranges are from about 0.1 μg/kg to about 10 mg/kg/day i.v., and from about 1 μg/kg to about 100 mg/kg/day p.o.

Methods of Therapy

The diazabicyclic aryl derivatives of the present invention are valuable nicotinic and monoamine receptor modulators, and therefore useful for the treatment of a range of ailments involving cholinergic dysfunction as well as a range of disorders responsive to the action of nAChR modulators.

In another aspect the invention provides a method for the treatment, prevention or alleviation of a disease or a disorder or a condition of a living animal body, including a human, which disease, disorder or condition is responsive to modulation of cholinergic receptors and/or monoamine receptors, and which method comprises administering to such a living animal body, including a human, in need thereof an effective amount of a diazabicyclic aryl derivative of the invention.

In a preferred embodiment, the disease, disorder or condition relates to the central nervous system.

In a preferred embodiment, the disease, disorder or condition is anxiety, cognitive disorders, learning deficit, memory deficits and dysfunction, Alzheimer's disease, attention deficit, attention deficit hyperactivity disorder, Parkinson's disease, Huntington's disease, Amyotrophic Lateral Sclerosis, Gilles de la Tourette's syndrome, depression, mania, manic depression, schizophrenia, obsessive compulsive disorders (OCD), panic disorders, eating disorders such as anorexia nervosa, bulimia and obesity, narcolepsy, nociception, AIDS-dementia, senile dementia, periferic neuropathy, autism, dyslexia, tardive dyskinesia, hyperkinesia, epilepsy, bulimia, post-traumatic syndrome, social phobia, sleeping disorders, pseudodementia, Ganser's syndrome, pre-menstrual syndrome, late luteal phase syndrome, chronic fatigue syndrome, mutism, trichotillomania, and jet-lag.

In a another preferred embodiment, the disease, disorder or condition are associated with smooth muscle contractions, including convulsive disorders, angina pectoris, premature labour, convulsions, diarrhoea, asthma, epilepsy, tardive dyskinesia, hyperkinesia, premature ejaculation, and erectile difficulty.

In a third preferred embodiment, the disease, disorder or condition is related to the endocrine system, such as thyrotoxicosis, pheochromocytoma, hypertension and arrhythmias.

In a fourth preferred embodiment, the disease, disorder or condition is a neurodegenerative disorders, including transient anoxia and induced neuro-degeneration.

In a sixth preferred embodiment, the disease, disorder or condition is an inflammatory disorder, including inflammatory skin disorders such as acne and rosacea, Chron's disease, inflammatory bowel disease, ulcerative colitis, and diarrhoea.

In a seventh preferred embodiment, the disease, disorder or condition is mild, moderate or even severe pain of acute, chronic or recurrent character, as well as pain caused by migraine, postoperative pain, and phantom limb pain.

In an eight preferred embodiment, the disease, disorder or condition is associated with withdrawal symptoms caused by termination of use of addictive substances, including nicotine-containing products such as tobacco, opioids such as heroin, cocaine and morphine, benzodiazepines and benzodiazepine-like drugs, and alcohol.

It is at present contemplated that suitable dosage ranges are 0.1 to 1000 milligrams daily, 10-500 milligrams daily, and especially 30-100 milligrams daily, dependent as usual upon the exact mode of administration, form in which administered, the indication toward which the administration is directed, the subject involved and the body weight of the subject involved, and further the preference and experience of the physician or veterinarian in charge.

A satisfactory result can, in certain instances, be obtained at a dosage as low as 0.005 mg/kg i.v. and 0.01 mg/kg p.o. The upper limit of the dosage range is about 10 mg/kg i.v. and 100 mg/kg p.o. Preferred ranges are from about 0.001 to about 1 mg/kg i.v. and from about 0.1 to about 10 mg/kg p.o.

EXAMPLES

The invention is further illustrated with reference to the following examples, which are not intended to be in any way limiting to the scope of the invention as claimed.

Example 1

Preparatory Example

All reactions involving air sensitive reagents or intermediates were performed under nitrogen and in anhydrous solvents. Magnesium sulphate was used as drying agent in the workup-procedures and solvents were evaporated under reduced pressure.

Diethyl meso-2,6-dibromopimeloate (Intermediate Compound 1)

Pimelic acid (240 g, 1.5 mol) was placed into a two-necked round bottom flask (1000 ml) fitted with a reflux condenser and an argon inlet. The reflux condenser was connected with two consecutive flasks (500 and 1000 ml). The first flask (500 ml) was placed in to dry ice-isopropanol vessel and the second was half filled with water for HCl absorption. Thionyl chloride (368 g, 3.09 mol) was added in three portions (180, 100 and 88 g) and stirred at 40° C. until gas elution ceased. Finally temperature was raised to 100° C., the first flask with liquid $SO_2$ was disconnected. The flask was fitted with dropping funnel and gas outlet. During 3 hours the flask was continuously irradiated with 300 W UV lamp and bromine (490 g, 3.06 mol) was added drop-wise. The HBr formed was absorbed in two consecutive water filled flasks (2×1000 ml). When HBr elution ceased, the dropping funnel was filled with absolute ethanol (200 ml) and carefully added drop-wise. The chilled solution was washed with water, aqueous sodium acetate and sodium thiosulfate. The separated organic phase was dried over sodium sulfate, filtrated and distilled in multiple portions (about 40 ml each) by a Büchi oven in vacua (0.5-1.0 mbar) at 150° C. collecting the fraction from the third flask. Yield: 487 g (87%).

Diethyl cis-1-Methylpiperidine-2,6-dicarboxylate (Intermediate Compound 2)

Diethyl meso-2,6-dibromoadipoate (1) (236 g, 0.631 mol) was placed into a two necked round bottom flask (2000 ml) fitted with a reflux condenser and a thermometer, and was dissolved in absolute THF (400 ml) under argon. A solution of methylamine (62 g, 2.0 mol) in absolute THF (400 ml) was added to the solution of compound 1. The flask was placed in cold water, to prevent it from warming. The reaction mixture was stirred for 18 hours under argon, the separated N-methylammonium bromide was removed by filtration and washed thoroughly with THF. The filtrate was concentrated on a rotary evaporator under reduced pressure and the residue (156 g) was distilled in four portions (about 39 g each) by a Büchi oven in vacuo (0.1-0.4 mbar) at 125° C. (average distillation time 1 hour) collecting the fraction from the third flask. Yield of compound 2 127.5 g (83%) as a light-yellowish oil.

3-Benzyl-9-methyl-3,9-diazabicyclo[3.3.1]nonane-2,4-dione (Intermediate Compound 3)

A solution of diethyl cis-1-methylpiperidin-2,6-carboxylate (127.5 g, 0.524 mol) and benzylamine (57.8 g, 0.540 mol) in xylene (150 ml) was refluxed in a round-bottomed flask (250 ml) for 44 hours. The latter was equipped with a vertical air condenser (15 cm) followed by a Liebig condenser, allowing removal of ethanol from the reaction mixture. The xylene was removed under reduced pressure through a Liebig condenser, the oil bath temperature was elevated to 205° C. and the mixture was heated under argon for 20 hours. The obtained product was distilled in four portions (about 45 g each) by a Büchi oven in vacuo (0.1 mbar) at 160° C. (average distillation time 1 hours) collecting the fraction from the third flask. The three combined $3^{rd}$ fractions (96 g) were dissolved by boiling in 50 ml of ethyl acetate and allowed to crystallize at room temperature for 3 days. The crystalline material was filtered off, washed with a small amount of ethyl acetate and dried in vacuo to afford 39.5 g of the product as a white crystalline solid. The filtrate was concentrated and the residue crystallized from ethyl acetate (30 ml) at 4° C. for 2 days to yield 6.2 g of the same product. Yield of compound 3 was 45.7 g (34%), mp. 117-118° C.

3-Benzyl-9-methyl-3,9-diazabicyclo[3.3.1]nonane (Intermediate Compound 4)

To a solution of compound 3 (45.7 g, 0.177 mol) in 1,4-dioxane (400 ml) placed into a three-necked round bottom flask (1000 ml), $LiAlH_4$ (9.0 g, 0.237 mol) was added in small portions and the mixture was refluxed under argon for 18 hours. The reaction mixture was cooled to 80° C. and a mixture of water (9 ml) and 1,4-dioxane (40 ml) was dropped carefully into reaction flask (caution: vigorous hydrogen evolution). A fine suspension was cooled to room temperature and treated with KOH solution (20 g in 50 ml of water). The organic phase was decanted and concentrated was concentrated under reduced pressure. The residue was distilled on Büchi oven in vacuo (0.1 mbar) at 130° C. The third collecting flask contained 3,9-diazabicyclo[3.3.1]nonane 4 (29.2 g, 72%) as a viscous colourless oil.

9-Methyl-3,9-diazabicyclo[3.3.1]nonane (Intermediate Compound 5)

To a solution of compound 4 (28.7 g, 0.125 mol) in absolute ethanol (100 ml) was added 10% Pd/C catalyst (6.3 g) under argon. The solution was hydrogenated with $H_2$ at 60 bar and 100° C. for 16 hours. The solution was filtered of on a Büchner funnel, the filtrate was concentrated under reduced pressure on a rotary evaporator and the residue distilled on Büchi oven in vacuo (0.1 mbar) at 100° C. to afford compound 5 (8.5 g, 49%) as a colourless gel.
Reference related to preparation of intermediate compounds 1-5: *Il Farmaco* 55 (8), August 2000, Pages 553-562.

Method A

9-Methyl-3-(6-phenyl-pyridazin-3-yl)-3,9-diazabicyclo[3.3.1]nonane Fumaric Acid Salt (Compound A1)

A mixture of 9-methyl-3,9-diazabicyclo[3.3.1]nonane (1.00 g, 7.13 mmol) and 3-chloro-6-phenylpyridazine (1.36 g 7.13 mmol) was stirred at 120° C. for 2.5 hours. Aqueous sodium hydroxide (50 ml, 1M) was added and the mixture was extracted twice with dichloromethane (2×50 ml). Chromatography on silica gel with dichloromethane, 10% methanol and 1% aqueous ammonia as solvent gave the title compound as a crystalline solid. Yield 870 mg (41%). The corresponding salt was obtained by addition of a diethyl ether and methanol mixture (9:1) saturated with fumaric acid. Mp. 187-188° C.

3-(6-Phenyl-pyridazin-3-yl)-3,9-diaza-bicyclo[3.3.1]nonane Free Base (Compound A2)

Was prepared according to reaction-conditions of Method A from 9-tert-butoxycarbonyl-3,9-diazabicyclo[3.3.1]nonane and 3-chloro-6-phenylpyridazine at 130° C. for 3 days, followed by treatment with TFA. Workup procedure was done according to Method A. LC-ESI-HRMS of [M+H]+ shows 281.1761 Da. Calc. 281.176621 Da, dev. −1.9 ppm.

9-Methyl-3-(5-phenyl-[1,3,4]oxadiazol-2-yl)-3,9-diaza-bicyclo[3.3.1]nonane Fumaric Acid Salt (Compound A3)

Was prepared according to Method A from 9-methyl-3,9-diazabicyclo[3.3.1]nonane and 2-phenyl-5-thiobenzyl[1,3,4]oxadiazole as reactants. Reaction time 8 h. LC-ESI-HRMS of [M+H]+ shows 285.173 Da. Calc. 285.171536 Da, dev. 5.1 ppm.

9-Methyl-3-(5-phenyl-[1,3,4]thiadiazol-2-yl)-3,9-diaza-bicyclo[3.3.1]nonane Fumaric Acid Salt (Compound A4)

Was prepared according to Method A from 9-methyl-3,9-diazabicyclo[3.3.1]nonane and 2-chloro-5-phenyl[1,3,4]oxadiazole as reactants. LC-ESI-HRMS of [M+H]+ shows 301.15 Da. Calc. 301.148692 Da, dev. 4.3 ppm.

3-[5-(4-Chloro-phenyl)-[1,3,4]thiadiazol-2-yl]-9-methyl-3,9-diaza-bicyclo[3.3.1]nonane Free Base (Compound A5)

Was prepared according to Method A from 9-methyl-3,9-diazabicyclo[3.3.1]nonane and 2-chloro-5-(4-chlorophenyl) [1,3,4]oxadiazole as reactants. LC-ESI-HRMS of [M+H]+ shows 335.1079 Da. Calc. 335.10972 Da, dev. −5.4 ppm.

Method B

3-(6-Iodo-pyridazin-3-yl)-9-methyl-9-aza-bicyclo [3.3.1]nonane Free Base (Intermediate Compound)

A mixture of 9-methyl-3,9-diazabicyclo[3.3.1]nonane (4.0 g, 28.5 mmol), 3,6-diiodopyridazine (9.5 g, 28.5 mmol), diisopropylethylamine (7.4 g, 57.0 mmol) and dioxane (50 ml) was stirred at 75° C. for 4 days. Aqueous sodium hydroxide (75 ml, 1 M) was added, dioxane was evaporated and the mixture was extracted twice with dichloromethane (2×75 ml). Chromatography on silica gel with dichloromethane, 10% methanol and 1% aqueous ammonia as solvent gave the title compound. Yield 4.61 g (47%). Mp 163-166° C.

3-(5-Bromopyrimidine-2-yl)-9-methyl-9-aza-bicyclo [3.3.1]nonane Free Base (Intermediate Compound)

Was prepared according to Method B from 9-methyl-3,9-diazabicyclo[3.3.1]nonane and 5-bromo-2-chloropyrimidine. LC-ESI-HRMS of [M+H]+ shows 297.0702 Da. Calc. 297.071484 Da, dev. −4.3 ppm.

Method C

9-Methyl-3-(6-thiophen-3-yl)-pyridazin-3-yl)-3,9-diaza-bicyclo[3.3.1]nonane Fumaric Acid Salt (Compound C1)

A mixture of 3-(6-iodo-pyridazin-3-yl)-9-methyl-9-aza-bicyclo[3.3.1]nonane free base (0.50 g, 1.45 mmol), 3-thiopheneboronic acid (0.28 g, 2.18 mmol), potassium carbonate (0.61 g, 4.36 mmol), palladacycle (27 mg, 0.029 mmol), 1,3-propandiol (0.31 ml, 4.3 mmol), 1,2-dimethoxyethane (20 ml) and water (2.2 ml) was stirred at reflux for 1 week. Aqueous sodium hydroxide (20 ml, 1 M) was added and the mixture was extracted twice with dichloromethane (2×30 ml). Chromatography on silica gel with dichloromethane, 10% methanol and 1% aqueous ammonia as solvent gave the title compound as a crystalline solid. Yield 100 mg (23%). The corresponding salt was obtained by addition of a diethyl ether and methanol mixture (9:1) saturated with fumaric acid. LC-ESI-HRMS of [M+H]+ shows 301.1497 Da. Calc. 301.148692 Da, dev. 3.3 ppm.

9-Methyl-3-(6-thiophen-2-yl-pyridazin-3-yl)-3,9-diaza-bicyclo[3.3.1]nonane Fumaric Acid Salt (Compound C2)

Was prepared according to Method C from 2-thiopheneboronic acid. LC-ESI-HRMS of [M+H]+ shows 301.1482 Da. Calc. 301.148692 Da, dev. −1.6 ppm.

3-(6-Furan-2-yl-pyridazin-3-yl)-9-methyl-3,9-diaza-bicyclo[3.3.1]nonane Fumaric Acid Salt (Compound C3)

Was prepared according to Method C from 2-furanboronic acid. LC-ESI-HRMS of [M+H]+ shows 285.1721 Da. Calc. 285.171536 Da, dev. 2 ppm.

3-(6-Furan-3-yl-pyridazin-3-yl)-9-methyl-3,9-diaza-bicyclo[3.3.1]nonane Fumaric Acid Salt (Compound C4)

Was prepared according to Method C from 3-furanboronic acid. LC-ESI-HRMS of [M+H]+ shows 285.1712 Da. Calc. 285.171536 Da, dev. −1.2 ppm.

3-[6-(3-Fluoro-phenyl)-pyridazin-3-yl]-9-methyl-3, 9-diaza-bicyclo[3.3.1]nonane Fumaric Acid Salt (Compound C5)

Was prepared according to Method C from 3-fluorobenzeneboronic acid. LC-ESI-HRMS of [M+H]+ shows 313.1822 Da. Calc. 313.182849 Da, dev. −2.1 ppm.

3-[6-(4-Fluoro-phenyl)-pyridazin-3-yl]-9-methyl-3, 9-diaza-bicyclo[3.3.1]nonane Fumaric Acid Salt (Compound C6)

Was prepared according to Method C from 4-fluorobenzeneboronic acid. LC-ESI-HRMS of [M+H]+ shows 313.1826 Da. Calc. 313.182849 Da, dev. −0.8 ppm.

3-[6-(2-Methoxy-phenyl)-pyridazin-3-yl]-9-methyl-3,9-diaza-bicyclo[3.3.1]nonane Fumaric Acid Salt (Compound C7)

Was prepared according to Method C from 2-methoxybenzeneboronic acid. LC-ESI-HRMS of [M+H]+ shows 325.2039 Da. Calc. 325.202836 Da, dev. 3.3 ppm.

3-[6-(3-Methoxy-phenyl)-pyridazin-3-yl]-9-methyl-3,9-diaza-bicyclo[3.3.1]nonane Fumaric Acid Salt (Compound C8)

Was prepared according to Method C from 3-methoxybenzeneboronic acid. LC-ESI-HRMS of [M+H]+ shows 325.2036 Da. Calc. 325.202836 Da, dev. 2.3 ppm.

3-[6-(2-Fluoro-phenyl)-pyridazin-3-yl]-9-methyl-3, 9-diaza-bicyclo[3.3.1]nonane Free Base (Compound C9)

Was prepared according to Method C from 2-fluorobenzeneboronic acid. LC-ESI-HRMS of [M+H]+ shows 313.1824 Da. Calc. 313.182849 Da, dev. −1.4 ppm.

3-[6-(4-Methoxy-phenyl)-pyridazin-3-yl]-9-methyl-3,9-diaza-bicyclo[3.3.1]nonane Fumaric Acid Salt (Compound C10)

Was prepared according to Method C from 4-methoxybenzeneboronic acid. LC-ESI-HRMS of [M+H]+ shows 325.2026 Da. Calc. 325.202836 Da, dev. −0.7 ppm.

3-[6-(9-Methyl-3,9-diaza-bicyclo[3.3.1]non-3-yl)-pyridazin-3-yl]-phenylamine Fumaric Acid Salt (Compound C11)

Was prepared according to Method C from 3-aminobenzeneboronic acid. LC-ESI-HRMS of [M+H]+ shows 310.2027 Da. Calc. 310.20317 Da, dev. −1.5 ppm.

3-[6-(5-Chloro-thiophen-2-yl)-pyridazin-3-yl]-9-methyl-3,9-diaza-bicyclo[3.3.1]nonane Fumaric Acid Salt (Compound C12)

Was prepared according to Method C from 5-chlorothiphene-2-boronic acid. LC-ESI-HRMS of [M+H]+ shows 335.1089 Da. Calc. 335.10972 Da, dev. −2.4 ppm.

9-Methyl-3-[6-(1H-pyrrol-2-yl)-pyridazin-3-yl]-3,9-diaza-bicyclo[3.3.1]nonane Free Base (Compound C13)

Was prepared according to the reaction-conditions of Method C from 1-tert-butoxycarbonyl-pyrrole-2-boronic acid, followed by deprotection with TFA, followed by the reaction-conditions of Method C. LC-ESI-HRMS of [M+H]+ shows 284.1887 Da. Calc. 284.18752 Da, dev. 4.2 ppm.

3[6-(1H-Indol-5-yl)-pyridazin-3-yl]-9-methyl-3,9-diaza-bicyclo[3.3.1]nonane Fumaric Acid Salt (Compound C14)

Was prepared according to the reaction-conditions of Method C from 5-(1H-indole)-boronic acid. LC-ESI-HRMS of [M+H]+ shows 334.2028 Da. Calc. 334.20317 Da, dev. −1.1 ppm.

3-(6-Benzol[1,3]dioxol-5-yl-pyridazin-3-yl)-9-methyl-3,9-diaza-bicyclo[3.3.1]nonane Fumaric Acid Salt (Compound C15)

Was prepared according to the reaction-conditions of Method C 5-benzo[1,3]dioxoleboronic acid. LC-ESI-HRMS of [M+H]+ shows 339.1826 Da. Calc. 339.182101 Da, dev. 1.5 ppm.

3-[6-(2,3-Dihydro-benzo[1,4]dioxin-6-yl)-pyridazin-3-yl]-9-methyl-3,9-diaza-bicyclo[3.3.1]nonane Fumaric Acid Salt (Compound C16)

Was prepared according to the reaction-conditions of Method C from 6-(2,3-dihydro-benzo[1,4]dioxineboronic acid. LC-ESI-HRMS of [M+H]+ shows 353.1977 Da. Calc. 353.197751 Da, dev. −0.1 ppm.

3-[6-(4-Chloro-phenyl)-pyridazin-3-yl]-9-methyl-3, 9-diaza-bicyclo[3.3.1]nonane Fumaric Acid Salt (Compound C17)

Was prepared according to the reaction-conditions of Method C from 4-chloro-benzeneboronic acid.

3-[6-(3-Chloro-phenyl)-pyridazin-3-yl]-9-methyl-3, 9-diaza-bicyclo[3.3.1]nonane Fumaric Acid Salt (Compound C18)

Was prepared according to the reaction-conditions of Method C from 3-chlorobenzeneboronic acid.

9-Methyl-3-(6-naphthalen-2-yl-pyridazin-3-yl)-3,9-diaza-bicyclo[3.3.1]nonane (Compound C19)

Was prepared according to the reaction-conditions of Method C from 2-naphthaleneboronic acid. LC-ESI-HRMS of [M+H]+ shows 345.2068 Da. Calc. 345.207921 Da, dev. −3.2 ppm.

3-(6-Benzofuran-2-yl-pyridazin-3-yl)-9-methyl-3,9-diaza-bicyclo[3.3.1]nonane (Compound C20)

Prepared according to the reaction-conditions of Method C from 2-benzofuranboronic acid. LC-ESI-HRMS of [M+H]+ shows 335.1873 Da. Calc. 335.187186 Da, dev. 0.3 ppm.

3-(6-Benzo[b]thiophen-2-yl-pyridazin-3-yl)-9-methyl-3,9-diaza-bicyclo[3.3.1]nonane (Compound C21)

Are prepared according to the reaction-conditions of Method C from 2-benzothiopheneboronic acid.

3[6-(3,4-Difluoro-phenyl)-pyridazin-3-yl]-9-methyl-3,9-diaza-bicyclo[3.3.1]nonane (Compound C22)

Prepared according to the reaction-conditions of Method C from 3,4-difluorobenzeneboronic acid. LC-ESI-HRMS of [M+H]+ shows 331.1726 Da. Calc. 331.173427 Da, dev. −2.5 ppm

3-[6-(2,3-Difluoro-phenyl)-pyridazin-3-yl]-9-methyl-3,9-diaza-bicyclo[3.3.1]nonane (Compound C23)

Was prepared according to the reaction-conditions of Method C from 2,3-difluorobenzeneboronic acid. LC-ESI-HRMS of [M+H]+ shows 331.1739 Da. Calc. 331.173427 Da, dev. 1.4 ppm.

3-[6-(3,4-Dimethoxy-phenyl)-pyridazin-3-yl]-9-methyl-3,9-diaza-bicyclo[3.3.1]nonane (Compound C24)

Are prepared according to the reaction-conditions of Method C from 3,4-dimethoxybenzeneboronic acid.

3-[6-(2,3-Dimethoxy-phenyl)-pyridazin-3-yl]-9-methyl-3,9-diaza-bicyclo[3.3.1]nonane (Compound C25)

Are prepared according to the reaction-conditions of Method C from 2,3-dimethoxybenzeneboronic acid.

9-Methyl-3-[6-(4-trifluoromethyl-phenyl)-pyridazin-3-yl]-3,9-diaza-bicyclo[3.3.1]nonane (Compound C26)

Are prepared according to the reaction-conditions of Method C from 4-trifluoromethylbenzeneboronic acid.

9-Methyl-3-[6-(3-trifluoromethyl-phenyl)-pyridazin-3-yl]-3,9-diaza-bicyclo[3.3.1]nonane (Compound C27)

Are prepared according to the reaction-conditions of Method C from 3-trifluoromethylbenzeneboronic acid.

9-Methyl-3-(5-thiophen-2-yl-pyrimidin-2-yl)-3,9-diaza-bicyclo[3.3.1]nonane Fumaric Acid Salt (Compound C28)

Was prepared from 3-(5-bromopyrimidine-2-yl)-9-methyl-9-aza-bicyclo[3.3.1]nonane free base and 2-thiopheneboronic acid according to Method C. LC-ESI-HRMS of [M+H]+ shows 301.1495 Da. Calc. 301.148692 Da, dev. 2.7 ppm.

9-Methyl-3-(5-thiophen-3-yl-pyrimidin-2-yl)-3,9-diaza-bicyclo[3.3.1]nonane Fumaric Acid Salt (Compound C29)

Was prepared from 3-(5-bromopyrimidine-2-yl)-9-methyl-9-aza-bicyclo[3.3.1]nonane free base and 3-thiopheneboronic acid according to Method C. LC-ESI-HRMS of [M+H]+ shows 301.149 Da. Calc. 301.148692 Da, dev. 1 ppm.

3-(5-Furan-3-yl-pyrimidin-2-yl)-9-methyl-3,9-diaza-bicyclo[3.3.1]nonane Fumaric Acid Salt (Compound C30)

Was prepared from 3-(5-bromopyrimidine-2-yl)-9-methyl-9-aza-bicyclo[3.3.1]nonane free base and 3-furanboronic acid according to Method C. LC-ESI-HRMS of [M+H]+ shows 285.1706 Da. Calc. 285.171536 Da, dev. −3.3 ppm.

3-(5-Furan-2-yl-pyrimidin-2-yl)-9-methyl-3,9-diaza-bicyclo[3.3.1]nonane Fumaric Acid Salt (Compound C31)

Was prepared from 3-(5-bromopyrimidine-2-yl)-9-methyl-9-aza-bicyclo[3.3.1]nonane free base and 2-furanboronic acid according to Method C. LC-ESI-HRMS of [M+H]+ shows 285.1704 Da. Calc. 285.171536 Da, dev. −4 ppm.

9-Methyl-3-(5-phenyl-pyrimidin-2-yl)-3,9-diaza-bicyclo[3.3.1]nonane (Compound C32)

Was prepared from 3-(5-bromopyrimidine-2-yl)-9-methyl-9-aza-bicyclo[3.3.1]nonane free base and benzeneboronic acid according to Method C. LC-ESI-HRMS of [M+H]+ shows 295.1909 Da. Calc. 295.192271 Da, dev. −4.6 ppm.

9-Methyl-3-(5-naphthalen-2-yl-pyrimidin-2-yl)-3,9-diaza-bicyclo[3.3.1]nonane (Compound C33)

Was prepared from 3-(5-bromopyrimidine-2-yl)-9-methyl-9-aza-bicyclo[3.3.1]nonane free base and 2-naphthaleneboronic acid according to Method C. LC-ESI-HRMS of [M+H]+ shows 345.2064 Da. Calc. 345.207921 Da, dev. −4.4 ppm.

3-(5-Benzofuran-2-yl-pyrimidin-2-yl)-9-methyl-3,9-diaza-bicyclo[3.3.1]nonane (Compound C34)

Are prepared from 3-(5-bromopyrimidine-2-yl)-9-methyl-9-aza-bicyclo[3.3.1]nonane free base and 2-benzofuranboronic acid according to Method C.

3-[5-(1H-Indol-5-yl)-pyrimidin-2-yl]-9-methyl-3,9-diaza-bicyclo[3.3.1]nonane (Compound C35)

Are prepared from 3-(5-bromopyrimidine-2-yl)-9-methyl-9-aza-bicyclo[3.3.1]nonane free base and 5-(1H-indol)-boronic acid according to Method C.

Method D

9-Ethyl-3-(6-phenyl-pyridazin-3-yl)-3,9-diaza-bicyclo[3.3.1]nonane Free Base (Compound D1)

A mixture of 3-(6-phenyl-pyridazin-3-yl)-3,9-diaza-bicyclo[3.3.1]nonane free base (0.20 g, 0.71 mmol), bromoethane (0.059 ml, 0.78 mmol), N,N-diisopropylethylamine (0.18 g, 1.42 mmol) and dimethylformamide (5 ml) was stirred at 80° C. for 2 hours. Aqueous sodium hydroxide (20 ml, 1 M) was added and the mixture was extracted twice with diethylether (2×20 ml). Chromatography on silica gel with dichloromethane, 10% methanol and 1% aqueous ammonia as solvent gave the title compound as a crystalline solid. LC-ESI-HRMS of [M+H]+ shows 281.1761 Da. Calc. 281.176621 Da, dev. −1.9 ppm.

9-(2-Methoxy-ethyl)-3-(6-phenyl-pyridazin-3-yl)-3, 9-diaza-bicyclo[3.3.1]nonane Fumaric Acid Salt (Compound D2)

Was prepared according to Method D from 2-bromoethyl-methylether. The corresponding salt was obtained by addition of a diethyl ether and methanol mixture (9:1) saturated with fumaric acid. LC-ESI-HRMS of [M+H]+ shows 339.2186 Da. Calc. 339.218486 Da, dev. 0.3 ppm.

9-Isopropyl-3-(6-phenyl-pyridazin-3-yl)-3,9-diaza-bicyclo[3.3.1]nonane Fumaric Acid Salt (Compound D3)

Was prepared according to Method D from 2-bromopropane. The corresponding salt was obtained by addition of a diethyl ether and methanol mixture (9:1) saturated with fumaric acid. LC-ESI-HRMS of [M+H]+ shows 323.2251 Da. Calc. 323.223571 Da, dev, 4.7 ppm.

9-Allyl-3-(6-phenyl-pyridazin-3-yl)-3,9-diaza-bicyclo[3.3.1]nonane Fumaric Acid Salt (Compound D4)

Was prepared according to Method D from 3-bromo-1-propene. The corresponding salt was obtained by addition of a diethyl ether and methanol mixture (9:1) saturated with fumaric acid. LC-ESI-HRMS of [M+H]+ shows 321.2094 Da. Calc. 321.207921 Da, dev. 4.6 ppm.

Method E

9,9-Dimethyl-3-(6-phenyl-pyridazin-3-yl)-3,9-diaza-bicyclo[3.3.1]nonane Onium Iodide Salt (Compound E1)

Was prepared by adding a mixture iodomethane (0.48, 3.4 mmol) to a solution of 9-methyl-3-(6-phenyl-pyridazin-3-yl)-3,9-diaza-bicyclo[3.3.1]nonane (1.0 g, 3.4 mmol) and dichloromethane (20 ml) and dicloromethane at −70° C. The mixture was stirred at −70° C. for 1 hour, followed by stirring at room-temperature for 10 days. The crude mixture was evaporated and diethylether (30 ml) was added followed by stirring and filtration. Yield 1.16 g (78%). LC-ESI-HRMS of M+ shows 309.2065 Da. Calc. 309.2079 Da, dev. −4.5 ppm.

Example 2

In Vitro Inhibition of $^3$H-α-Bungarotoxine Binding in Rat Brain

In this example the affinity of the compounds of the invention for binding to $\alpha_7$-subtype of nicotinic receptors is determined.

α-Bungarotoxine is a peptide isolated from the venom of the Elapidae snake *Bungarus multicinctus*. It has high affinity for neuronal and neuromuscular nicotinic receptors, where it acts as a potent antagonist.

$^3$H-α-Bungarotoxine labels nicotinic acetylcholine receptors formed by the $\alpha_7$ subunit isoform found in brain and the $\alpha_1$ isoform in the neuromuscular junction.

Tissue Preparation

Preparations are performed at 0-4° C. Cerebral cortices from male Wistar rats (150-250 g) are homogenised for 10 seconds in 15 ml of 20 mM Hepes buffer containing 118 mM NaCl, 4.8 mM KCl, 1.2 mM $MgSO_4$ and 2.5 mM $CaCl_2$ (pH 7.5) using an Ultra-Turrax homogeniser. The tissue suspension is subjected to centrifugation at 27,000×g for 10 minutes. The supernatant is discarded and the pellet is washed twice by centrifugation at 27,000×g for 10 minutes in 20 ml of fresh buffer, and the final pellet is then re-suspended in fresh buffer containing 0.01% BSA (35 ml per g of original tissue) and used for binding assays.

Assay

Aliquots of 500 µl of homogenate are added to 25 µl of test solution and 25 µl of $^3$H-α-bungarotoxine (2 nM, final concentration) and mixed and incubated for 2 hours at 37° C. Non-specific binding is determined using (−)-nicotine (1 mM, final concentration). After incubation, the samples are added 5 ml of ice-cold Hepes buffer containing 0.05% PEI and poured directly onto Whatman GF/C glass fibre filters (pre-soaked in 0.1% PEI for at least 6 hours) under suction, and immediately washed with 2×5 ml ice-cold buffer.

The amount of radioactivity on the filters is determined by conventional liquid scintillation counting. Specific binding is total binding minus non-specific binding.

The test value is given as an $IC_{50}$ (the concentration of the test substance which inhibits the specific binding of $^3$H-α-bungarotoxin by 50%).

When subjected to this test the compounds of the invention, exemplified by e.g. Compounds A1, C1 and D1, show results in the sub-micro-molar (i.e. <1 µM) level.

The invention claimed is:

1. A diazabicyclic aryl derivative represented by Formula I

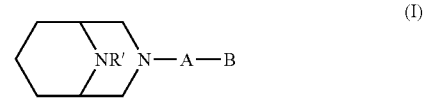

any of its stereoenantiomers or any mixture of its stereoenantiomers, or a pharmaceutically acceptable salt thereof, wherein R' represents hydrogen, alkyl, alkenyl or alkoxy-alkyl;

A represents an aromatic monocyclic group selected from phenyl, furanyl, thienyl, selenophenyl, pyrrolyl, oxazolyl, thiazolyl, imidazolyl, pyrazolyl, isoxazolyl, isothiazolyl, oxadiazolyl, triazolyl, thiadiazolyl, pyridinyl, pyridazinyl, pyrimidinyl, pyrazinyl and triazinyl; and B represents an aromatic monocyclic or bicyclic carbocyclic or heterocyclic group, which carbocyclic or heterocyclic groups are optionally substituted one or more times with substituents selected from the group consisting of alkyl, cycloalkyl, cycloalkyl-alkyl, hydroxy, alkoxy, cyanoalkyl, halo, trihaloalkyl, trihaloalkoxy, cyano, nitro, amino, alkyl-carbonyl-amino, methylenedioxy and ethylenedioxy.

2. The diazabicyclic aryl derivative of claim 1, or a pharmaceutically acceptable salt thereof, wherein R' represents hydrogen, or alkyl, alkenyl or alkoxy-alkyl.

3. The diazabicyclic aryl derivative of claim 2, or a pharmaceutically acceptable salt thereof, wherein R' represents alkyl.

4. The diazabicyclic aryl derivative of claim 1, or a pharmaceutically acceptable salt thereof, wherein A represents an aromatic monocyclic group selected from phenyl, furanyl, thienyl, selenophenyl, pyrrolyl, oxazolyl, thiazolyl, imidazolyl, pyrazolyl, isoxazolyl, isothiazolyl, oxadiazolyl, triazolyl, thiadiazolyl, pyridinyl, pyridazinyl, pyrimidinyl, pyrazinyl and triazinyl.

5. The diazabicyclic aryl derivative of claim 4, or a pharmaceutically acceptable salt thereof, wherein A represents an aromatic heterocyclic group selected from furanyl, thienyl, selenophenyl, pyrrolyl, oxazolyl, thiazolyl, imidazolyl, pyrazolyl, isoxazolyl, isothiazolyl, oxadiazolyl, triazolyl, thiadiazolyl, pyridinyl, pyridazinyl, pyrimidinyl, pyrazinyl and triazinyl.

6. The diazabicyclic aryl derivative of claim 5, or a pharmaceutically acceptable salt thereof, wherein A represents oxazolyl, thiazolyl, oxadiazolyl, thiadiazolyl, pyridinyl, pyridazinyl, pyrimidinyl or pyrazinyl.

7. The diazabicyclic aryl derivative of claim 1, or a pharmaceutically acceptable salt thereof, wherein B represents an aromatic monocyclic or bicyclic carbocyclic or heterocyclic group, which carbocyclic or heterocyclic groups are optionally substituted one or more times with substituents selected from the group consisting of alkyl, cycloalkyl, cycloalkyl-alkyl, hydroxy, alkoxy, cyanoalkyl, halo, trihaloalkyl, trihaloalkoxy, cyano, nitro, amino, alkyl-carbonyl-amino, methylenedioxy and ethylenedioxy.

8. The diazabicyclic aryl derivative of claim 7, or a pharmaceutically acceptable salt thereof, wherein B represents an aromatic monocyclic or bicyclic carbocyclic or heterocyclic group selected from phenyl, naphthyl, pyrrolyl, furanyl, thienyl, indolyl, benzofuranyl and benzothienyl, which carbocyclic or heterocyclic groups are optionally substituted one or more times with substituents selected from the group consisting of alkyl, cycloalkyl, cycloalkyl-alkyl, hydroxy, alkoxy, cyanoalkyl, halo, trihaloalkyl, trihaloalkoxy, cyano, nitro, amino, alkyl-carbonyl-amino, methylenedioxy and ethylenedioxy.

9. The diazabicyclic aryl derivative of claim 8, or a pharmaceutically acceptable salt thereof, wherein B represents phenyl or naphthyl, which phenyl and naphthyl are unsubstituted or substituted once or twice with halo, alkoxy and/or amino, or substituted with methylenedioxy or with ethylenedioxy.

10. The diazabicyclic aryl derivative of claim 8, or a pharmaceutically acceptable salt thereof, wherein B represents pyrrolyl, furanyl or thienyl, which pyrrolyl, furanyl or thienyl are unsubstituted or substituted once with halo.

11. The diazabicyclic aryl derivative of claim 8, or a pharmaceutically acceptable salt thereof, wherein B represents indolyl, benzofuranyl and benzothienyl, which indolyl, benzofuranyl and benzothienyl are unsubstituted.

12. The diazabicyclic aryl derivative of claim 1, which is
9-Methyl-3-(6-phenyl-pyridazin-3-yl)-3,9-diaza-bicyclo[3.3.1]nonane;
3-(6-Phenyl-pyridazin-3-yl)-3,9-diaza-bicyclo[3.3.1]nonane;
9-Methyl-3-(5-phenyl-[1,3,4]oxadiazol-2-yl)-3,9-diaza-bicyclo[3.3.1]nonane;
9-Methyl-3-(5-phenyl-[1,3,4]thiadiazol-2-yl)-3,9-diaza-bicyclo[3.3.1]nonane;
3-[5-(4-Chloro-phenyl)-[1,3,4]thiadiazol-2-yl]-9-methyl-3,9-diaza-bicyclo[3.3.1]nonane;
9-Methyl-3-(6-thiophen-3-yl-pyridazin-3-yl)-3,9-diaza-bicyclo[3.3.1]nonane;
9-Methyl-3-(6-thiophen-2-yl-pyridazin-3-yl)-3,9-diaza-bicyclo[3.3.1]nonane;
3-(6-Furan-2-yl-pyridazin-3-yl)-9-methyl-3,9-diaza-bicyclo[3.3.1]nonane;
3-(6-Furan-3-yl-pyridazin-3-yl)-9-methyl-3,9-diaza-bicyclo[3.3.1]nonane;
3-[6-(3-Fluoro-phenyl)-pyridazin-3-yl]-9-methyl-3,9-diaza-bicyclo[3.3.1]nonane;
3-[6-(4-Fluoro-phenyl)-pyridazin-3-yl]-9-methyl-3,9-diaza-bicyclo[3.3.1]nonane;
3-[6-(2-Methoxy-phenyl)-pyridazin-3-yl]-9-methyl-3,9-diaza-bicyclo[3.3.1]nonane;
3-[6-(3-Methoxy-phenyl)-pyridazin-3-yl]-9-methyl-3,9-diaza-bicyclo[3.3.1]nonane;
3-[6-(2-Fluoro-phenyl)-pyridazin-3-yl]-9-methyl-3,9-diaza-bicyclo[3.3.1]nonane;
3-[6-(4-Methoxy-phenyl)-pyridazin-3-yl]-9-methyl-3,9-diaza-bicyclo[3.3.1]nonane;
3-[6-(9-Methyl-3,9-diaza-bicyclo[3.3.1]non-3-yl)-pyridazin-3-yl]-phenylamine;
3-[6-(5-Chloro-thiophen-2-yl)-pyridazin-3-yl]-9-methyl-3,9-diaza-bicyclo[3.3.1]nonane;
9-Methyl-3-[6-(1H-pyrrol-2-yl)-pyridazin-3-yl]-3,9-diaza-bicyclo[3.3.1]nonane;
3-[6-(1H-Indol-5-yl)-pyridazin-3-yl]-9-methyl-3,9-diaza-bicyclo[3.3.1]nonane;
3-(6-Benzo[1,3]dioxol-5-yl-pyridazin-3-yl)-9-methyl-3,9-diaza-bicyclo[3.3.1]nonane;
3-[6-(2,3-Dihydro-benzo[1,4]dioxin-6-yl)-pyridazin-3-yl]-9-methyl-3,9-diaza-bicyclo[3.3.1]nonane;
3-[6-(4-Chloro-phenyl)-pyridazin-3-yl]-9-methyl-3,9-diaza-bicyclo[3.3.1]nonane;
3-[6-(3-Chloro-phenyl)-pyridazin-3-yl]-9-methyl-3,9-diaza-bicyclo[3.3.1]nonane;
9-Methyl-3-(6-naphthalen-2-yl-pyridazin-3-yl)-3,9-diaza-bicyclo[3.3.1]nonane;
3-(6-Benzofuran-2-yl-pyridazin-3-yl)-9-methyl-3,9-diaza-bicyclo[3.3.1]nonane;
3-(6-Benzo[b]thiophen-2-yl-pyridazin-3-yl)-9-methyl-3,9-diaza-bicyclo[3.3.1]nonane;
3-[6-(3,4-Difluoro-phenyl)-pyridazin-3-yl]-9-methyl-3,9-diaza-bicyclo[3.3.1]nonane;
3-[6-(2,3-Difluoro-phenyl)-pyridazin-3-yl]-9-methyl-3,9-diaza-bicyclo[3.3.1]nonane;
3-[6-(3,4-Dimethoxy-phenyl)-pyridazin-3-yl]-9-methyl-3,9-diaza-bicyclo[3.3.1]nonane;
3-[6-(2,3-Dimethoxy-phenyl)-pyridazin-3-yl]-9-methyl-3,9-diaza-bicyclo[3.3.1]nonane;
9-Methyl-3-[6-(4-trifluoromethyl-phenyl)-pyridazin-3-yl]-3,9-diaza-bicyclo[3.3.1]nonane;
9-Methyl-3-[6-(3-trifluoromethyl-phenyl)-pyridazin-3-yl]-3,9-diaza-bicyclo[3.3.1]nonane;
9-Methyl-3-(5-thiophen-2-yl-pyrimidin-2-yl)-3,9-diaza-bicyclo[3.3.1]nonane;
9-Methyl-3-(5-thiophen-3-yl-pyrimidin-2-yl)-3,9-diaza-bicyclo[3.3.1]nonane;
3-(5-Furan-3-yl-pyrimidin-2-yl)-9-methyl-3,9-diaza-bicyclo[3.3.1]nonane;
3-(5-Furan-2-yl-pyrimidin-2-yl)-9-methyl-3,9-diaza-bicyclo[3.3.1]nonane;
9-Methyl-3-(5-phenyl-pyrimidin-2-yl)-3,9-diaza-bicyclo[3.3.1]nonane;

9-Methyl-3-(5-naphthalen-2-yl-pyrimidin-2-yl)-3,9-diaza-bicyclo[3.3.1]nonane;

3-(5-Benzofuran-2-yl-pyrimidin-2-yl)-9-methyl-3,9-diaza-bicyclo[3.3.1]nonane;

3-[5-(1H-Indol-5-yl)-pyrimidin-2-yl]-9-methyl-3,9-diaza-bicyclo[3.3.1]nonane;

9-Ethyl-3-(6-phenyl-pyridazin-3-yl)-3,9-diaza-bicyclo[3.3.1]nonane;

9-(2-Methoxy-ethyl)-3-(6-phenyl-pyridazin-3-yl)-3,9-diaza-bicyclo[3.3.1]nonane;

9-Isopropyl-3-(6-phenyl-pyridazin-3-yl)-3,9-diaza-bicyclo[3.3.1]nonane;

9-Allyl-3-(6-phenyl-pyridazin-3-yl)-3,9-diaza-bicyclo[3.3.1]nonane; or 9,9-Dimethyl-3-(6-phenyl-pyridazin-3-yl)-3,9-diaza-bicyclo[3.3.1]nonane;

or an enantiomer or a mixture of its enantiomers, or a pharmaceutically acceptable salt thereof.

13. A pharmaceutical composition comprising a therapeutically effective amount of a diazabicyclic aryl derivative of claim 1, or a pharmaceutically-acceptable addition salt thereof, or a prodrug thereof, together with at least one pharmaceutically-acceptable carrier or diluent.

* * * * *

UNITED STATES PATENT AND TRADEMARK OFFICE
CERTIFICATE OF CORRECTION

PATENT NO.          : 8,173,658 B2
APPLICATION NO.     : 12/093655
DATED               : May 8, 2012
INVENTOR(S)         : Dan Peters et al.

It is certified that error appears in the above-identified patent and that said Letters Patent is hereby corrected as shown below:

On the Title Page, at item (54) and at column 1, lines 1-2, correct the title to read as follows:

--DIAZABICYCLIC ARYL DERIVATIVES AND THEIR MEDICAL USE--.

On the Title Page, insert the following information:

--Related U.S. Application Data

(60) Provisional application No. 60/748,222, filed on Dec. 8, 2005.--.

Signed and Sealed this
Fourteenth Day of August, 2012

David J. Kappos
*Director of the United States Patent and Trademark Office*